United States Patent
Jackman et al.

(10) Patent No.: US 6,469,175 B1
(45) Date of Patent: Oct. 22, 2002

(54) METHODS OF PURIFYING 2-METHYLTHIO-5-TRIFLUOROMETHYL-1,3,4-THIADIAZOLE

(75) Inventors: Dennis E. Jackman, Prairie Village, KS (US); Joe J. Hanson, Holt, MO (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/789,369

(22) Filed: Feb. 20, 2001

(51) Int. Cl.[7] .............................................. C07D 285/12
(52) U.S. Cl. ...................................................... 548/136
(58) Field of Search .......................................... 548/136

(56) References Cited

U.S. PATENT DOCUMENTS

| | | | |
|---|---|---|---|
| 5,898,074 A | 4/1999 | Prasad et al. | 548/136 |
| 6,005,114 A | 12/1999 | Prasad et al. | 548/136 |
| 6,034,245 A | 3/2000 | Prasad et al. | 548/136 |

*Primary Examiner*—Cecilia Tsang
*Assistant Examiner*—Ebenezer Sackey
(74) *Attorney, Agent, or Firm*—Joseph C. Gil; Raymond J. Harmuth

(57) ABSTRACT

Methods of purifying 2-methylthio-5-trifluoromethyl-1,3,4-thiadiazole include the steps of providing a first 2-methylthio-5-trifluoromethyl-1,3,4-thiadiazole composition comprising 2-methylthio-5-trifluoromethyl-1,3,4-thiadiazole and organic solvent; performing a first extraction of the 2-methylthio-5-trifluoromethyl-1,3,4-thiadiazole composition with a first inorganic acid solution; and performing a second extraction of the 2-methylthio-5-trifluoromethyl-1,3,4-thiadiazole composition with a second inorganic acid solution.

20 Claims, No Drawings

METHODS OF PURIFYING 2-METHYLTHIO-5-TRIFLUOROMETHYL-1,3,4-THIADIAZOLE

FIELD OF THE INVENTION

This invention relates to methods of purifying thiadiazoles. More particularly, this invention pertains to methods of purifying 2-(methylthio)-5-trifluoromethyl)-1,3,4-thiadiazole using multiple acid extractions.

BACKGROUND OF THE INVENTION

The reaction of methyldithiocarbazinate (MDTC) with trifluoroacetic acid (TFA) forms a mixture of 2-(methylthio)-5-(trifluoromethyl)-1,3,4-thiadiazole (TDA) and 2,5-bis-(methylthio)-1,3,4-thiadiazole (bis by-product). Unfortunately, it is often difficult to remove the bis by-product from the resulting mixture without undesirable losses of TDA.

Prasad et al., U.S. Pat. No. 5,898,074, disclose a process of making 2-(methylthio)-5-(trifluoromethyl)-1,3,4-thiadiazole comprising the steps of reacting methyldithiocarbazinate with a molar excess of trifluoroacetic acid in the absence of phosphoryl chloride, wherein the molar ratio of trifluoroacetic acid to methyldithiocarbazinate is from about 1.1:1 to about 5:1 and water is a by-product of reaction; and recovering the excess trifluoroacetic acid. Prasad et al. teach that the organic phase of the reaction mixture is mixed with 70 wt % sulfuric acid to protonize the major impurity and extract it into the aqueous phase.

Prasad et al., U.S. Pat. No. 6,005,114, disclose a process of making 2-(methylthio)-5-(trifluoromethyl)-1,3,4-thiadiazole comprising the steps of reacting methyldithiocarbazinate and trifluoroacetic acid in a molar ratio of methyldithiocarbazinate to trifluoroacetic acid of from about 4:1 to about 1:5 and in the absence of phosphorus trichloride to form a mixture of 2-(methylthio)-5-(trifluoromethyl)-1,3,4-thiadiazole and 2,5-bis-(methylthio)-1,3,4-thiadiazole; and selectively removing the 2,5-bis-(methylthio)-1,3,4-thiadiazole by acidification of the reaction mixture followed by phase separation.

Prasad et al., U.S. Pat. No. 6,034,245 disclose a process of making 2-(methylthio)-5-(trifluoromethyl)-1,3,4-thiadiazole comprising the steps of reacting methyldithiocarbazinate with trifluoroacetic acid in the absence of phosphorus trichloride to form a mixture of 2-(methylthio)-5-(trifluoromethyl)-1,3,4-thiadiazole and 2,5-bis-(methylthio)-1,3,4-thiadiazole, wherein the molar ratio of methyldithiocarbazinate to trifluoroacetic acid is from about 4:1 to about 1:5 and the mixture contains a first organic phase and a first aqueous phase. Prasad et al. teach separating the first organic phase and the first aqueous phase; acidifying the first organic phase with a concentrated inorganic acid, resulting in the formation of a second organic phase and a second aqueous phase, wherein the 2,5-bis-(methylthio)-1,3,4-thiadiazole is soluble in the second aqueous phase; and separating the second organic phase and the second aqueous phase, wherein the 2,5-bis-(methylthio)-1,3,4-thiadiazole remains in the second aqueous phase.

Unfortunately, it has been found that a single acid extraction of the organic phase of a 2-(methylthio)-5-(trifluoromethyl)-1,3,4-thiadiazole reaction mixture often results in poor yields and/or purity when utilized commercially. Thus, there is a need for processes for preparation or purification of 2-(methylthio)-5-(trifluoromethyl)-1,3,4-thiadiazole which result in good yields and/or purity when utilized commercially.

SUMMARY OF THE INVENTION

Accordingly, it is an object of the present invention to obviate problems of the prior art. It is a further object of the present invention to. provide methods of purifying 2-(methylthio)-5-(trifluoromethyl)-1,3,4-thiadiazole good yields and/or purity.

These and additional objects are provided by the methods of the invention.

In accordance with one aspect of the invention there are provided methods of purifying 2-methylthio-5-trifluoromethyl-1,3,4-thiadiazole comprising the steps of providing a first 2-methylthio-5-trifluoromethyl-1,3,4-thiadiazole composition comprising 2-methylthio-5-trifluoromethyl-1,3,4-thiadiazole and organic solvent; performing a first extraction of the 2-methylthio-5-trifluoromethyl-1,3,4-thiadiazole composition with a first inorganic acid solution; and performing a second extraction of the 2-methylthio-5-trifluoromethyl-1,3,4-thiadiazole composition with a second inorganic acid solution.

In accordance with another aspect of the invention there are provided methods of purifying 2-methylthio-5-trifluoromethyl-1,3,4-thiadiazole comprising the steps of providing a first composition comprising 2-methylthio-5-trifluoromethyl-1,3,4-thiadiazole and organic solvent and a second composition comprising 2-methylthio-5-trifluoromethyl-1,3,4-thiadiazole and organic solvent; performing a first extraction of the first composition with a first inorganic acid solution; performing a second extraction of the first composition with a second inorganic acid solution; performing a first extraction of the second composition with the second inorganic acid solution; and performing a second extraction of the second composition with a third inorganic acid solution.

In accordance with yet another aspect of the invention there are provided processes of making 2-(methylthio)-5-(trifluoromethyl)-1,3,4-thiadiazole. The processes comprise the steps of reacting methyldithiocarbazinate with trifluoroacetic acid thereby forming a reaction mixture; isolating a first organic phase from the reaction mixture; acidifying the first organic phase with a first inorganic acid solution, thereby forming a second organic phase and a second aqueous phase; separating the second organic phase and the second aqueous phase; acidifying the second organic phase with a second inorganic acid solution, thereby forming a third organic phase and a third aqueous phase; and separating the third organic phase and the third aqueous. The 2-(methylthio)-5-(trifluoromethyl)-1,3,4-thiadiazole is present in the third organic phase.

The methods of the invention of the invention are advantageous in that the TDA obtained is of high purity, and the amount of TDA loss during purification is decreased as compared to methods using a single acid extraction.

These and additional aspects, objects and advantages of the invention are more fully described in the following detailed description.

DETAILED DESCRIPTION

The reaction of methyldithiocarbazinate (MDTC) with trifluoroacetic acid (TFA) forms a mixture of 2-(methylthio)-5-(trifluoromethyl)-1,3,4-thiadiazole (TDA) and 2,5-bis-(methylthio)-1,3,4-thiadiazole (bis by-product). The reaction of MDTC with TFA forms a reaction mixture comprising an aqueous phase, which is removed from the reaction mixture by azeotropic distillation, and an organic phase. The TDA and bis by-product are contained in the organic phase.

While not being bound by theory, it is believed that both the bis by-product and the TDA form complexes with acid, and that the bis by-product can displace TDA from TDA-acid complexes. The displacement can be diagrammed in the reaction shown below:

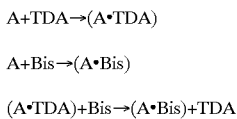

wherein "A" represents an acid, preferably an inorganic acid such as sulfuric acid, "(A•TDA)" represents a TDA-acid complex, and "(Bis•TDA)" represents a bis by-product-acid complex. The TDA-acid complex and bis by-product-acid complex are acid soluble, and thus may be removed from an organic phase with an acid solution, preferably an inorganic acid solution.

A single acid extraction often results is loss of TDA into the acid solution, or undesirable levels of bis by-product in the organic phase. It has unexpectedly been found that multiple acid extractions, particularly acid extractions wherein a first extraction is performed using an acid solution which was previously used in a prior extraction, results in improved yield and purity of TDA. As used herein, "acid extraction" refers to a process in which an organic phase is acidified with an acid solution, and as a result of acidification, a second organic phase and aqueous phase are formed. Thus "multiple acid extractions" refers to a process in which a second organic phase is obtained from the first acid extraction, and the second organic phase is subjected to at least one additional acid extraction, resulting in, for example, a third organic phase and aqueous phase from a second extraction; a fourth organic phase and aqueous phase from a third extraction; and so forth.

While not being bound by theory, an initial acid extraction of the organic phase from a first TDA reaction mixture is believed to result in an acid phase containing both (A•TDA) and (A•Bis) complexes. When this acid phase is separated from the organic phase of the first TDA reaction mixture, and is used in the first extraction of the organic phase from a subsequent TDA reaction mixture, the bis by-product in the organic phase of the subsequent reaction mixture displaces the TDA from the (A•TDA) of the acid phase, resulting in an acid phase with a significant amount of bis by-product and a low level of TDA. The subsequent TDA reaction mixture is extracted with a fresh acid solution (i.e. an acid solution which has not been used in a prior extraction) to give TDA of high yield and/or purity.

It has surprisingly been found that bis by-product removal is improved by using two acid extractions, rather than one acid extraction, of the organic phase of the reaction mixture. It has also surprisingly been found that the TDA yield obtained from a first extraction using an acid comprising both (A•TDA) and (A•Bis) complexes and a second extraction using an acid which is free of (A•TDA) and (A•Bis) complexes is greater that the yield obtained from a single extraction using an acid which is free of (A•TDA) and (A•Bis) complexes.

Generally, organic phases of TDA reaction mixtures treated in accordance with the present invention comprise from about 1 to about 5, preferably 1.5 to about 2.5%, by weight, of bis by-product. TDA purified in accordance with the present invention is generally obtained in yields of from about 99 to about 99.5%, preferably from about 99.3 to about 99.5%, and in a purity of from about 59 to about 63%, preferably from about 60 to about 62%. In one embodiment the TDA yield obtained from a first extraction using an acid comprising both (A•TDA) and (A•Bis) complexes and a second extraction using an acid which is free of (A•TDA) and (A•Bis) complexes is at least about 3% greater, preferably at least about 3.4% greater than the yield obtained from a single extraction using an acid which is free of (A•TDA) and (A•Bis) complexes.

Methods of preparing 2-(methylthio)-5-(trifluoromethyl)-1,3,4-thiadiazole by reacting methyldithiocarbazinate with trifluoroacetic acid are disclosed in U.S. Pat. Nos. 5,101,034, 5,162,539, 5,898,074, 5,905,157, 6,005,114, and 6,034,245, all incorporated herein by reference. In one embodiment the reaction of methyldithiocarbazinate with trifluoroacetic acid occurs in the presence of phosphoryl chloride, in another embodiment the reaction occurs in the presence of phosphorus trichloride, and in yet another embodiment the reaction occurs in the absence of phosphorus trichloride.

Any suitable ratio of methyldithiocarbazinate and trifluoroacetic acid may be used, and either reactant may be present in a molar excess. In one embodiment the molar ratio of methyldithiocarbazinate to trifluoroacetic acid is from about 4:1 to about 1:5, while in another embodiment the molar ratio of methyldithiocarbazinate to trifluoroacetic acid is from about 2:1 to about 1.5:1. In other embodiments the molar ratio of methyldithiocarbazinate to trifluoroacetic acid is from about 1.1:1 to about 5:1, from about 1.25:1 to about 2.5:1, or from about 1.25:1 to about 2:1.

The reaction of methyldithiocarbazinate with trifluoroacetic acid occurs in the presence of an organic solvent. The organic solvent may be the trifluoroacetic acid itself or may comprise an additional organic solvent, such as aprotic aromatic solvents. As used herein, "aprotic solvents" is intended to refer to solvents that do not dissociate to provide substantial and measurable proton concentrations. Suitable aprotic aromatic solvents include toluene, xylene, cumene or mesitylene. In one embodiment the reaction of methyldithiocarbazinate with trifluoroacetic acid occurs in the presence of toluene, thus the solvent comprises TFA and toluene.

In one embodiment an aprotic aromatic solvent present in an amount of from about 0.5 moles to about 3.5, preferably from about 1.5 to about 2.5, moles of aprotic aromatic solvent per mole of MDTC. In another embodiment, toluene is present in an amount of from about 0.5 moles to about 3.5 moles, preferably from about 1.5 moles to about 3.0 moles, more preferably from about 2.5 to about 3.0 moles, of toluene per mole of MDTC.

The reaction may proceed by mixing the entire desired amounts of MDTC and TFA. All other modes of addition are suitable as well. The reaction mixture of MDTC and TFA may optionally include a catalyst, such as p-toluene sulfonic acid. In one embodiment p-toluene sulfonic acid is present in an amount of about 2.0 grams per mole of MDTC.

The methyldithiocarbazinate and trifluoroacetic acid are combined at a temperature and for a time sufficient for the desire reaction to occur. In one embodiment the reaction temperature is from about 30° C. to about 150° C., preferably from about 30° C. to about 140° C. In another embodiment the reaction time is from about 1 to about 10, preferably from about 2 to about 6 hours. In another embodiment the reaction temperature is from about 80° C. to about 130° C., and the reaction time is from about 1 to about 5 hours.

The MDTC used in the present process may contain up to about 10 weight percent water. In one embodiment water is added as a separate reactant. The total amount of water in the reaction mixture is preferably less than about 30 grams of water per 0.5 moles of MDTC.

Water is formed as a reaction product of the TFA and MDTC. The water thus formed and any additional water present, referred to herein as "a first aqueous phase", is removed from the reaction mixture by an azeotropic distillation. While not being bound by theory, it is believed that the removal of the water formed during the reaction assists in driving the reaction toward completion. The azeotropic removal of water may be accomplished in the presence of solvent, such as toluene. The temperature required from the completion of the reaction is adequate for the azeotropic removal of the water and excess TFA.

After the azeotropic removal of water and excess TFA a first organic phase containing the TDA and bis by-product is obtained. The first organic phase may optionally be extracted with a basic solution. The first organic phase in then subjected to at least two acid extractions.

In one method in accordance with the present invention, the first organic phase is acidified with a first inorganic acid solution, thereby forming a second organic phase and a second aqueous phase. The second organic phase and the second aqueous phase are then separated, and the second organic phase is acidified with a second inorganic acid solution, thereby forming a third organic phase and a third aqueous phase. The third organic phase and the third aqueous phase are separated. The 2-(methylthio)-5-(trifluoromethyl)-1,3,4-thiadiazole is present in the third organic phase. The third organic phase may be a yellowish oil.

Preferably the acid solution comprises an inorganic acid, more preferably a concentrated inorganic acid. Suitable inorganic acids include phosphoric acid, hydrochloric acid (HCl), sulfuric acid ($H_2SO_4$) or nitric acid ($HNO_3$). Generally, the acid has a pKa of from about 1 to about 4. In one embodiment the acid is sulfuric acid. The sulfuric acid may have a concentration of from about 55% to about 95% and, preferably about 65% to about 75%, by weight. In one embodiment the sulfuric acid concentration is about 70%, by weight.

The molar ratio of total inorganic acid used in both the first and second extractions to 2,5-bis-methylthio-1,3,4-thiadiazole may be from about 3:1 to about 12:1; preferably from about 4:1 to about 6:1. Acidification typically occurs at a temperature of from about 10° C. to about 60° C., preferably from about 20° C. to about 40° C., more preferably from about 25° C. to about 30° C.

Preferably the inorganic acid solution used in the second extraction of the organic phase of a TDA reaction mixture is used in the first extraction of the organic phase of a subsequent TDA reaction mixture. The inorganic acid solution is generally discarded after this second use. Although the first extraction of the organic phase of the TDA reaction mixture is preferably performed with an inorganic acid solution used in a previous extraction, the second extraction of the organic phase is performed with an inorganic acid solution which has not been used in a previous extraction.

Throughout the examples and the present specification, parts and percentages are by weight unless otherwise specified. The following example is illustrative only and is not intended to limit the scope of the methods and fabrics of the invention as defined by the claims.

EXAMPLES

Example 1

To about 40 gm of TDA reaction mixture (containing, by weight, about 37% toluene, about 60.42% TDA and about 2.64% bis by-product) at room temperature is added sulfuric acid as indicated in Table 1 below. The acid layer is removed, and the organic layer analyzed by gas chromatography. The acid layer is weighed and mixed with about 20 times its volume of ice water and neutralized with sodium bicarbonate. The liberated organics are extracted from the acid layer/ice water mixture using chloroform and analyzed by gas chromatography. The percentages are calculated based on total weight of organic, thus the weight of the solvent is included when determining percentages.

TABLE 1

Single and Double Extraction of Bis By-Product from TDA Reaction Mixture

| sample number | % $H_2SO_4$ used | g $H_2SO_4$ used | mole ratio $H_2SO_4$: bis | % TDA in resulting organic layer | % bis by-product in resulting organic layer | % 4.2 min. peak | % 8.5 min. peak |
|---|---|---|---|---|---|---|---|
| 1 | — | 0 | — | 60.42 | 2.64 | 0.10 | 0 |
| 2 | 65 | 9.5 | 11:1 | 60.80 | 0.11 | 0 | 0 |
| 3a | 65 | 7.5 | 9:1 | 61.00 | 0.19 | 0 | 0 |
| 3b | 65 | 2.0 | 2:1 | 59.84 | 0 | 0 | 0 |
| 4 | 70 | 9.5 | 12:1 | 59.12 | 0.08 | 0 | 0 |
| 5a | 70 | 7.5 | 9.5:1 | 60.64 | 0.13 | 0 | 0 |
| 5b | 70 | 2.0 | 2.5:1 | 59:73 | 0 | 0 | 0 |

The columns labeled "% 4.2 min. peak" and "%8.5 min. peak" refer to impurity which, is present, may appear at 4.2 and 8.5 minutes of the gas chromatography.

Sample 1 is a sample of the TDA reaction mixture, while Samples 2 and 4 are sample treated with single extractions using 65% and 70%, by weight, sulfuric acid, respectively, in accordance with the prior art. Samples 3 and 5 are samples treated with multiple extractions using previously unused, or "fresh", sulfuric acid, in accordance with one embodiment of the invention. Samples 3a and 5a represent the first extractions, using 65% and 70%, by weight, sulfuric acid, respectively; while Samples 3b and 5b represent the second extractions, using 65% and 70%, by weight, sulfuric acid, respectively.

As indicated by the Sample 2, when a single extraction using 9.5 gm of 65% by weight, sulfuric acid is performed, the remaining organic layer still contains 0.11%, by weight, bis by-product. However, when the same amount of acid is divided into two serial extractions, the organic layer contains no detectable bis by-product following the second extraction, as indicated by Sample 3b. Similarly, when a single extraction using 9.5 gm of 70% by weight, sulfuric acid is performed, the remaining organic layer still contains 0.08%, by weight, bis by-product, as indicated by the Sample 4. However, when the same amount of acid is divided into two serial extractions, the organic layer contains no detectable bis by-product following the second extraction, as indicated by Sample 5b.

Example 2

To about 400 gm of the organic phase from a TDA reaction mixture (containing about 36.4% toluene, about 61.0% TDA, and about 1.9% bis by-product) at room temperature is added about 12.5 gm of 70% sulfuric acid. The mixture is stirred in a Morton (baffled) flask for 15 minutes, then allowed to stand for 15 minutes. The lower acid phase is removed through a bottom drain, and the organic phase analyzed by gas chromatography. Discarded acid phases, that is, acid phases which are not to be used in an additional extraction, are weighed and mixed with from about 20 to about 30 times their volume of ice water and then neutralized. The liberated organics from the acid phase/ice water mixture are dissolved in toluene or chloroform and analyzed by gas chromatography.

One organic phase, Sample 1, is extracted twice using previously unused, or "fresh", sulfuric acid. Another organic phase, Sample 2, is extracted a first time using the acid phase from the second extraction of Sample 1, and extracted a second time with fresh acid. The results of this treatment in accordance with one aspect of the invention are set forth below in Table 2. The percentages are calculated on a solvent free basis, that is, the toluene is not included when determining percentages.

TABLE 2

Serial Extraction Using Fresh and Previously Used Acid Solutions

| Sample | Phase | % TDA | % bis by-product |
|---|---|---|---|
| Sample 1 | T0 | 97.9 | 1.9 |
| | T1 | 98.4 | 1.3 |
| | 1st A1 | 9.6 | 87.7 |
| | T2 | 99.6 | 0.2 |
| | 2nd A1 | 31.2 | 64.6 |
| Sample 2 | T0 | 97.8 | 1.9 |
| | T1 | 97.4 | 2.3 |
| | 1st A2 (using 2nd A1 from sample 1) | 7.8 | 91.0 |
| | T2 | 99.2 | 0.5 |
| | 2nd A1 | 14.3 | 83.2 |

T0 = Unextracted TDA organic phase
T1 = TDA organic phase after one extraction
T2 = TDA organic phase after two extractions
A1 = $H_2SO_4$ after being used for one extraction
A2 = $H_2SO_4$ after being used for two extractions As indicated by the data set forth for Sample 1 in Table 2, after one extraction using "fresh" sulfuric acid, the organic phase contains 1.3%, by weight, bis by-product, and following a second extraction using fresh sulfuric acid the organic phase contains only 0.2%, by weight, bis by-product. The acid used in the first extraction contains 9.6%, by weight, TDA, and the acid used in the second extraction contains 31.2%, by weight TDA.

As indicated by the data set forth for Sample 2 in Table 2, after one extraction using the sulfuric acid used in the second extraction of Sample 1, the organic phase contains 2.3%, by weight, bis by-product, and following a second extraction using fresh sulfuric acid the organic phase contains only 0.5%, by weight, bis by-product. The acid used in the first extraction contains 7.8%, by weight, TDA, and the acid used in the second extraction contains 14.3%, by weight TDA.

Thus, the amount of TDA in the acid phase originally designated "2nd A1" dropped from 31.2% to 7.8% when that acid phase was used in the first extraction of Sample 2, indicating that TDA originally left behind in the acid phase of the second extraction of Sample 1 is recovered when that acid phase is used in the first extraction of Sample 2. Thus, treatment of samples in accordance with this embodiment of the invention increases overall TDA yield as compared to a single acid extraction.

Example 3

The process is repeated as above except about 16.5 gm of 70% sulfuric acid is used. The results are set forth below in Table 3. The percentages are calculated on a solvent free basis.

TABLE 3

Serial Extraction Using Fresh and Previously Used Acid

| Sample | Phase | % TDA | % bis by-product |
|---|---|---|---|
| Sample 1 | T0 | 97.9 | 1.9 |
| | T1 | 99.0 | 0.74 |
| | 1st A1 | 12.3 | 87.8 |
| | T2 | 99.8 | 0.1 |
| | 2nd A1 | 60.2 | 34.9 |
| Sample 2 | T0 | 97.9 | 1.9 |
| | T1 | 98.2 | 1.4 |
| | 1st A2 (using 2nd A1 from sample 1) | 11.8 | 85.8 |
| | T2 | 99.2 | 0.2 |
| | 2nd A1 | 39.8 | 54.8 |

T0 = Unextracted TDA organic phase
T1 = TDA organic phase after one extraction
T2 = TDA organic phase after two extractions
A1 = $H_2SO_4$ after being used for one extraction
A2 = $H_2SO_4$ after being used for two extractions As indicated by the data set forth for Sample 1 in Table 3, after two extractions using "fresh" sulfuric acid, the acid used in the first extraction contains 12.3%, by weight, TDA, and the acid used in the second extraction contains 60.2%, by weight TDA.

As indicated by the data set forth for Sample 2 in Table 3, after one extraction using the sulfuric acid used in the second extraction of Sample 1 and a second extraction using fresh sulfuric acid the acid used in the first extraction contains 11.8%, by weight, TDA, and the acid used in the second extraction contains 39.8%,. by weight TDA.

The data indicates that TDA originally left behind in the acid phase of the second extraction of Sample 1 is recovered when that acid phase is used in the first extraction of Sample 2. Thus, treatment of samples in accordance with this embodiment of the invention increases overall TDA yield as compared to a single acid extraction.

Example 4

The process is repeated as above except about 21.0 gm of 70% sulfuric acid is used. The results are set forth below in Table 4. The percentages are calculated on a solvent free basis.

TABLE 4

Serial Extraction Using Fresh and Previously Used Acid

| Sample | Phase | % TDA | % bis by-product |
|---|---|---|---|
| Sample 1 | T0 | 97.9 | 1.9 |
| | T1 | 99.2 | 0.5 |
| | 1st A1 | 20.0 | 80.0 |
| | T2 | 99.8 | 0.1 |
| | 2nd A1 | 78.4 | 17.7 |
| Sample 2 | T0 | 97.9 | 1.9 |
| | T1 | 98.8 | 0.7 |
| | 1st A2 (using 2nd A1 from sample 1) | 12.9 | 84.1 |
| | T2 | 99.7 | 0.1 |
| | 2nd A1 | 65.4 | 28.1 |

T0 = Unextracted TDA organic phase
T1 = TDA organic phase after one extraction
T2 = TDA organic phase after two extractions
A1 = $H_2SO_4$ after being used for one extraction
A2 = $H_2SO_4$ after being used for two extractions As indicated by the data set forth for Sample 1 in Table 4, after two extractions using "fresh" sulfuric acid, the acid used in the first extraction contains 20.0%, by weight, TDA, and the acid used in the second extraction contains 78.4%, by weight TDA.

As indicated by the data set forth for Sample 2 in Table 4, after one extraction using the sulfuric acid used in the second extraction of Sample 1 and a second extraction using fresh sulfuric acid the acid used in the first extraction contains 12.9%, by weight, TDA, and the acid used in the second extraction contains 65.%, by weight TDA.

The data indicates that TDA originally left behind in the acid phase of the second extraction of Sample 1 is recovered when that acid phase is used in the first extraction of Sample 2. Thus, treatment of samples in accordance with this embodiment of the invention increases overall TDA yield as compared to a single acid extraction.

Additional embodiments and modifications within the scope of the claimed invention will be apparent to one of ordinary skill in the art. Accordingly, the scope of the present invention shall be considered in terms of the following claims, and is understood not to be limited to the details of the methods described in the specification.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of separating 2-methylthio-5-trifluoromethyl-1,3,4-thiadiazole from 2,5-bis-methylthio-1,3,4-thiadiazole in one or more compositions containing both said 2-methylthio-5-trifluoromethyl-1,3,4-thiadiazole and said 2,5-bis-methylthio-1,3,4-thiadiazole in an organic solvent, with minimal loss of said 2-methylthio-5-trifluoromethyl-1,3,4-thiadiazole comprising the steps of:
   (a) providing a first composition, said first composition comprising 2-methylthio-5-trifluoromethyl-1,3,4-thiadiazole and 2,5-bis-methylthio-1,3,4-thiadiazole in an organic solvent, said first composition not having been previously subjected to an extraction with an inorganic acid solution to remove said 2,5-bis-methylthio-1,3,4-thiadiazole;
   (b) performing a first extraction of said first composition with a first inorganic acid solution to remove at least a portion of said 2,5-bis-methylthio-1,3,4-thiadiazole from said first composition, wherein said first inorganic acid solution had, prior to said performing step, been used to extract 2,5-bis-methylthio-1,3,4-thiadiazole from a second composition, said second composition comprising 2-methylthio-5-trifluoromethyl-1,3,4-thiadiazole and 2,5-bis-methylthio-1,3,4-thiadiazole in an organic solvent, said first inorganic acid solution having a higher proportion of 2-methylthio-5-trifluoromethyl-1,3,4-thiadiazole than 2,5-bis-methylthio-1,3,4-thiadiazole, whereupon in performing said first extraction, an organic phase and an inorganic phase are formed, wherein at least a portion of said 2,5-bis-methylthio-1,3,4-thiadiazole is removed from said first composition into said inorganic phase and where said inorganic phase has a higher proportion of 2,5-bis-methylthio-1,3,4-thiadiazole than 2-methylthio-5-trifluoromethyl-1,3,4-thiadiazole;
   (c) separating said organic phase from said inorganic phase; and
   (d) performing a second extraction on said separated organic phase with a second inorganic acid solution, said second inorganic acid solution not having been previously used in an extraction of a composition comprising 2-methylthio-5-trifluoromethyl-1,3,4-thiadiazole and 2,5-bis-methylthio-1,3,4-thiadiazole in an organic solvent, whereupon a second organic phase and a second inorganic phase are formed, wherein the 2,5-bis-methylthio-1,3,4-thiadiazole content of said second organic phase is less than 0.1 percent by weight of TDA.

2. A method according to claim 1, wherein the first and second inorganic acid solutions each independently comprise an acid selected from the group consisting of phosphoric acid, hydrochloric acid, nitric acid and sulfuric acid.

3. A method according to claim 2, wherein the first and second inorganic acid solutions each comprise sulfuric acid.

4. A method according to claim 3, wherein the first and second inorganic acid solutions each comprise from about 55% to about 95%, by weight, sulfuric acid.

5. A method according to claim 1, further comprising the step of performing a first extraction of a third composition, said third composition comprising 2-methylthio-5-trifluoromethyl-1,3,4-thiadiazole and 2,5-bis-methylthio-1,3,4-thiadiazole in an organic solvent, said first extraction of said third composition being performed with said second inorganic acid solution after said second inorganic acid solution has been used to perform said second extraction.

6. A method according to claim 5, wherein the second inorganic acid solution is discarded after said first extraction of said third composition.

7. A method according to claim 1, wherein the organic solvent comprises an aprotic aromatic solvent.

8. A method according to claim 1, wherein the molar ratio of total inorganic acid used in the first extraction to 2,5-bis-methylthio-1,3,4-thiadiazole is from about 3:1 to about 12:1.

9. A method of separating 2-methylthio-5-trifluoromethyl-1,3,4-thiadiazole from 2,5-bis-methylthio-1,3,4-thiadiazole in one or more compositions containing both said 2-methylthio-5-trifluoromethyl-1,3,4-thiadiazole and said 2,5-bis-methylthio-1,3,4-thiadiazole in an organic solvent, with minimal loss of said 2-methylthio-5-trifluoromethyl-1,3,4-thiadiazole comprising the steps of:
   (a) providing a first composition comprising 2-methylthio-5-trifluoromethyl-1,3,4-thiadiazole, 2,5-bis-methylthio-1,3,4-thiadiazole and an organic solvent and a second composition comprising 2-methylthio-5- trifluoromethyl-1,3,4-thiadiazole, 2,5-bis-methylthio-1,3,4-thiadiazole and an organic solvent;

(b) performing a first extraction of the first composition with a first inorganic acid solution to remove at least a portion of said 2,5-bis-methylthio-1,3,4-thiadiazole from said first composition, said first inorganic acid solution not having been used in a previous 2-methylthio-5-trifluoromethyl-1,3,4-thiadiazole extraction, whereupon a first organic phase and a first inorganic phase are formed during said extraction;

(c) separating said first organic phase from said first inorganic phase;

(d) performing a second extraction on said separated first organic phase of the first composition with a second inorganic acid solution, said second inorganic acid solution not having been used in a previous 2-methylthio-5-trifluoromethyl-1,3,4-thiadiazole extraction, whereupon a second organic phase and a second inorganic phase are formed, said second organic phase having a 2,5-bis-methylthio-1,3,4-thiadiazole content below about 0.1% and said second inorganic phase having a higher proportion of 2-methylthio-5-trifluoromethyl-1,3,4-thiadiazole than 2,5-bis-methylthio-1,3,4-thiadiazole;

(e) performing a first extraction of said second composition with said second inorganic phase, whereupon a third organic phase and a third inorganic phase are formed, wherein said third inorganic phase has a higher proportion of 2,5-bis-methylthio-1,3,4-thiadiazole than 2-methylthio-5-trifluoromethyl-1,3,4-thiadiazole;

(f) separating said third organic phase from said third inorganic phase (g) performing a second extraction of said third organic phase of the second composition with a third inorganic acid solution, said third inorganic acid solution not having been used in a previous 2-methylthio-5-trifluoromethyl-1,3,4-thiadiazole extraction, whereupon a fourth organic phase and a fourth inorganic phase are formed, said fourth organic phase having a 2,5-bis-methylthio-1,3,4-thiadiazole content of less than about 0.1 % by weight.

10. A method according to claim 9, further comprising the steps of:

(h) providing a third composition comprising 2-methylthio-5-trifluoromethyl-1,3,4-thiadiazole and organic solvent;

(i) performing a first extraction of the third composition with said fourth inorganic phase, said fourth inorganic phase having a higher proportion of 2-methylthio-5-trifluoromethyl-1,3,4-thiadiazole than 2,5-bis-methylthio-1,3,4-thiadiazole, whereupon a fifth organic phase and a fifth inorganic phase are formed, wherein said fifth inorganic phase has a higher proportion of 2,5-bis-methylthio-1,3,4-thiadiazole than 2-methylthio-5-trifluoromethyl-1,3,4-thiadiazole; and (j) performing a second extraction of said fifth organic phase of the third composition with a fourth inorganic acid solution said fourth inorganic acid solution not having been used in a previous 2-methylthio-5-trifluoromethyl-1,3,4-thiadiazole extraction, whereupon a sixth organic phase and a sixth inorganic phase are formed, said sixth organic phase having a 2,5-bis-methylthio-1,3,4-thiadiazole content of less than about 0.1% by weight.

11. A method according to claim 9, wherein the first, second and third inorganic acid solutions each comprise sulfuric acid.

12. A method according to claim 11, wherein the first, second and third inorganic acid solutions each comprise from about 55% to about 95%, by weight, sulfuric acid.

13. A method of making 2-(methylthio)-5-(trifluoromethyl)-1,3,4-thiadiazole comprising the steps of:

(a) reacting methyldithiocarbazinate with trifluoroacetic acid, thereby forming a reaction mixture;

(b) isolating a first organic phase from the reaction mixture;

(c) acidifying the first organic phase with a first inorganic acid solution, said first inorganic acid solution having been used in a previous 2-methylthio-5-trifluoromethyl-1,3,4-thiadiazole extraction, thereby forming a second organic phase and a second aqueous phase;

(d) separating the second organic phase and the second aqueous phase;

(e) acidifying the second organic phase with a second inorganic acid solution, said second inorganic acid solution not having been used in a previous 2-methylthio-5-trifluoromethyl-1,3,4-thiadiazole extraction thereby forming a third organic phase and a third aqueous phase; and (f) separating the third organic phase and the third aqueous phase.

14. A method according to claim 13, wherein the method removes 2,5-bis-methylthio-1,3,4-thiadiazole from the 2-methylthio-5-trifluoromethyl-1,3,4-thiadiazole composition.

15. A method according to claim 13, wherein step (a) occurs in the presence of phosphoryl chloride.

16. A method according to claim 13, wherein step (a) occurs in the presence of phosphorus trichloride.

17. A method according to claim 13, wherein step (a) occurs in the absence of phosphorus trichloride.

18. A method according to claim 13, wherein the molar ratio of the total inorganic acid used in step (c) to the 2,5-bis-methylthio-1,3,4-thiadiazole is from about 3:1 to about 12:1.

19. A method according to claim 13, wherein the first and second inorganic acid solutions each comprise from about 55% to about 95%, by weight, sulfuric acid.

20. A method according to claim 13, wherein the step of isolating the first organic phase from the reaction mixture comprises the step of removing a first aqueous phase from the reaction mixture by azeotropic distillation.

\* \* \* \* \*